(12) United States Patent
Gladnick et al.

(10) Patent No.: US 10,341,646 B2
(45) Date of Patent: Jul. 2, 2019

(54) VARIABLE FOCAL LENGTH LENS SYSTEM WITH OPTICAL POWER MONITORING

(71) Applicant: Mitutoyo Corporation, Kanagawa-ken (JP)

(72) Inventors: Paul Gerard Gladnick, Seattle, WA (US); Robert Kamil Bryll, Bothell, WA (US)

(73) Assignee: Mitutoyo Corporation, Kawasaki-shi, Kanagawa-ken (JP)

( * ) Notice: Subject to any disclaimer, the term of this patent is extended or adjusted under 35 U.S.C. 154(b) by 104 days.

(21) Appl. No.: 15/721,112

(22) Filed: Sep. 29, 2017

(65) Prior Publication Data
US 2019/0104302 A1   Apr. 4, 2019

(51) Int. Cl.
*G02F 1/33* (2006.01)
*H04N 17/00* (2006.01)
*H04N 5/235* (2006.01)

(52) U.S. Cl.
CPC ............ *H04N 17/002* (2013.01); *G02F 1/33* (2013.01); *H04N 5/2353* (2013.01)

(58) Field of Classification Search
CPC ....... H04N 17/002; H04N 5/2353; G02F 1/33
See application file for complete search history.

(56) References Cited

U.S. PATENT DOCUMENTS

| | | | |
|---|---|---|---|
| 6,542,180 B1 | 4/2003 | Wasserman et al. | |
| 7,324,682 B2 | 1/2008 | Wasserman | |
| 7,454,053 B2 | 11/2008 | Bryll et al. | |
| 7,627,162 B2 | 12/2009 | Blanford et al. | |
| 8,111,905 B2 | 2/2012 | Campbell | |
| 8,111,938 B2 | 2/2012 | Bryll et al. | |
| 9,143,674 B2 | 9/2015 | Gladnick | |
| 9,720,218 B2 | 8/2017 | Cui et al. | |
| 9,736,355 B1 | 8/2017 | Bryll | |
| 10,171,725 B1 * | 1/2019 | Nahum | H04N 5/23212 |
| 2013/0148196 A1 | 6/2013 | Arnold | |

(Continued)

OTHER PUBLICATIONS

Extended European Search Report, dated Dec. 10, 2018, for European Application No. 18197601.0-1022, 6 pages.

(Continued)

*Primary Examiner* — John R Schnurr
(74) *Attorney, Agent, or Firm* — Seed IP Law Group LLP

(57) ABSTRACT

A variable focal length (VFL) lens system is provided including a VFL lens, a VFL lens controller, an objective lens, a camera and an optical power monitoring configuration. During a standard workpiece imaging mode, the objective lens transmits workpiece light along an imaging optical path through the VFL lens to the camera, which provides a corresponding workpiece image exposure. During an optical power monitoring mode, the optical power monitoring configuration produces a monitored beam pattern which travels along at least a portion of the imaging optical path through the VFL lens to the camera, which provides a monitoring image exposure. Different monitoring image exposures are acquired at different phase timings of the periodic modulation of the VFL lens, and a dimension of the monitored beam pattern is measured in each monitoring image exposure as related to an optical power of the VFL lens at the corresponding phase timing.

20 Claims, 7 Drawing Sheets

(56) References Cited

U.S. PATENT DOCUMENTS

2014/0368726 A1* 12/2014 Gladnick ........... G01B 11/0608
348/349
2015/0042992 A1* 2/2015 Cui ...................... G02B 21/002
356/369
2018/0088440 A1* 3/2018 Gladnick ........... G01N 21/8806

OTHER PUBLICATIONS

Mermillod-Blondin et al., "High-speed varifocal imaging with a tunable acoustic gradient index of refraction lens," *Optics Letters* 33(18):2146-2148.

Mitutoyo Corporation & Micro Encoder Inc. "QVPAK® 3D CNC Vision Measuring Machine," User's Guide, Version 7, 2003, 329 pages.

Mitutoyo Corporation & Micro Encoder Inc. "QVPAK® 3D CNC Vision Measuring Machine," Operation Guide, Version 2.0, 1996, 86 pages.

\* cited by examiner

VARIABLE FOCAL LENGTH LENS SYSTEM WITH OPTICAL POWER MONITORING

BACKGROUND

Technical Field

This disclosure relates to precision metrology using a high speed variable focal length lens (e.g., in a machine vision inspection system), and more particularly to monitoring the optical power of a high speed variable focal length lens in an imaging system.

Description of the Related Art

Precision non-contact metrology systems such as precision machine vision inspection systems (or "vision systems" for short) may be utilized to obtain precise dimensional measurements of objects and to inspect various other object characteristics, and may include a computer, a camera and optical system, and a precision stage that moves to allow workpiece traversal and inspection. One exemplary prior art system is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, and the QVPAK 3D CNC Vision Measuring Machine Operation Guide, published September 1996, each of which is hereby incorporated by reference in its entirety. This type of system uses a microscope-type optical system and moves the stage so as to provide inspection images of either small or relatively large workpieces.

General-purpose precision machine vision inspection systems are generally programmable to provide automated video inspection. Such systems typically include GUI features and predefined image analysis "video tools" such that operation and programming can be performed by "non-expert" operators. For example, U.S. Pat. No. 6,542,180, which is incorporated herein by reference in its entirety, teaches a vision system that uses automated video inspection including the use of various video tools.

Multi-lens variable focal length (VFL) optical systems may be utilized in an imaging system for observation and precision measurement of surface heights. The imaging system may be included in a microscope system and/or in a precision machine vision inspection system, for example as disclosed in U.S. Pat. No. 9,143,674, which is hereby incorporated herein by reference in its entirety. Briefly, a VFL lens is capable of acquiring multiple images at multiple focal lengths, respectively. One type of known VFL lens is a tunable acoustic gradient ("TAG") lens. A TAG lens is a high speed VFL lens that creates a lensing effect using sound waves in a fluid medium. The sound waves may be created by application of an electrical field at a resonant frequency to a piezoelectric tube surrounding the fluid medium. The sound waves create a time-varying density and index of refraction profile in the lens's fluid, which modulates its optical power and focal length or focus position. A TAG lens may periodically sweep a range of focal lengths at a resonant frequency of up to several hundred kHz, i.e., at a high speed. Such a lens may be understood in greater detail by the teachings of the article, "High speed varifocal imaging with a tunable acoustic gradient index of refraction lens" (*Optics Letters*, Vol. 33, No. 18, Sep. 15, 2008), which is hereby incorporated herein by reference in its entirety. Tunable acoustic gradient index lenses and related controllable signal generators are available, for example, from TAG Optics, Inc., of Princeton, N.J. The Model TL2.B.xxx series lenses, for example, are capable of modulation up to approximately 600 kHz.

While such VFL lenses are able to be periodically modulated and change focus position at a very high rate, variations in conditions such as temperature may give rise to changes in optical power and modulation frequency, which may affect system performance and accuracy. An imaging system that is able to provide improvements with regard to such issues would be desirable.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A variable focal length (VFL) lens system is provided including a VFL lens, a VFL lens controller, an objective lens, a camera and an optical power monitoring configuration OPM. In various implementations, the VFL lens may be a tunable acoustic gradient index of refraction (TAG) lens. The VFL lens controller controls the VFL lens to periodically modulate the optical power of the VFL lens over a range of optical powers at an operating frequency. The objective lens inputs workpiece light arising from a workpiece surface during a workpiece imaging mode and transmits the workpiece light along an imaging optical path that passes through the VFL lens. The camera receives the workpiece light transmitted by the VFL lens along the imaging optical path during the workpiece imaging mode and provides a corresponding workpiece image exposure.

The optical power monitoring configuration includes a monitoring beam generator comprising a light source and a beam pattern element that inputs light from the light source and outputs a monitored beam pattern. In various implementations, the optical power monitoring configuration transmits the monitored beam pattern along at least a portion of the imaging optical path to travel through the VFL lens to the camera during an optical power monitoring mode. The camera provides a monitoring image exposure including the monitored beam pattern during a corresponding phase timing of the periodic modulation of the VFL lens during the optical power monitoring mode. A dimension of the monitored beam pattern in the monitoring image exposure is related to an optical power of the VFL lens during the corresponding phase timing.

In various implementations, different monitoring image exposures may be acquired at different phase timings of the periodic modulation of the VFL lens (e.g., at phase timings corresponding to 0 degrees, 180 degrees and 90 degrees). A dimension of the monitored beam pattern in each monitoring image exposure may be measured and comparisons may be made to calibration values. Based on the comparisons, adjustments may be made to the system (e.g., adjustments may be made to the operation of the VFL lens to cause the optical power of the VFL lens to more closely approximate calibration levels).

DETAILED DESCRIPTION

Figure 1:
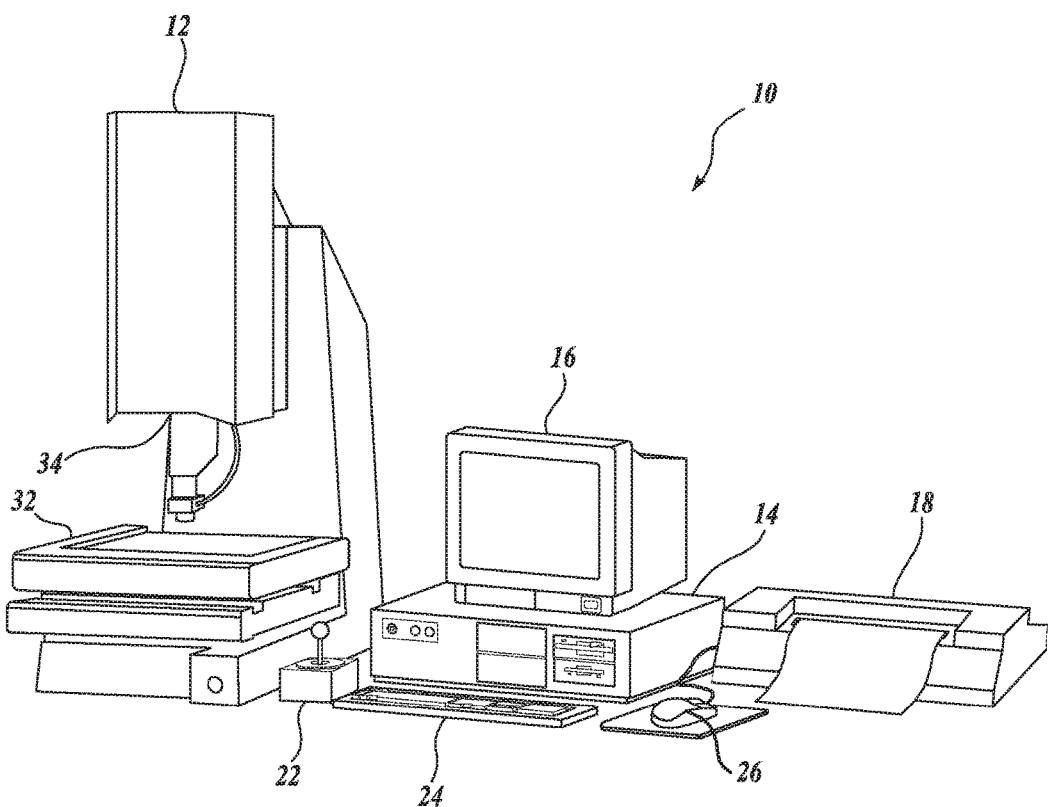
FIG. 1 is a diagram showing various typical components of a general-purpose precision machine vision inspection system.

FIG. 1 is a block diagram of one exemplary machine vision inspection system 10 usable as an imaging system in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10. It will be appreciated that in various implementations, a touch-screen tablet or the like may be substituted for and/or redundantly provide the functions of any or all of the computer system 14, the display 16, the joystick 22, the keyboard 24, and the mouse 26.

Those skilled in the art will appreciate that the controlling computer system 14 may generally consist of any computing system or device. Suitable computing systems or devices may include personal computers, server computers, minicomputers, mainframe computers, distributed computing environments that include any of the foregoing, and the like. Such computing systems or devices may include one or more processors that execute software to perform the functions described herein. Processors include programmable general-purpose or special-purpose microprocessors, programmable controllers, application-specific integrated circuits (ASICs), programmable logic devices (PLDs), or the like, or a combination of such devices. Software may be stored in memory, such as random-access memory (RAM), read-only memory (ROM), flash memory, or the like, or a combination of such components. Software may also be stored in one or more storage devices, such as optical-based disks, flash memory devices, or any other type of non-volatile storage medium for storing data. Software may include one or more program modules that include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 that may include a zoom lens or interchangeable lenses. The zoom lens or interchangeable lenses generally provide various magnifications for the images provided by the optical imaging system 34. Various implementations of the machine vision inspection system 10 are also described in commonly assigned U.S. Pat. Nos. 7,454,053; 7,324,682; 8,111,905; and 8,111,938, each of which is hereby incorporated herein by reference in its entirety.

Figure 2:
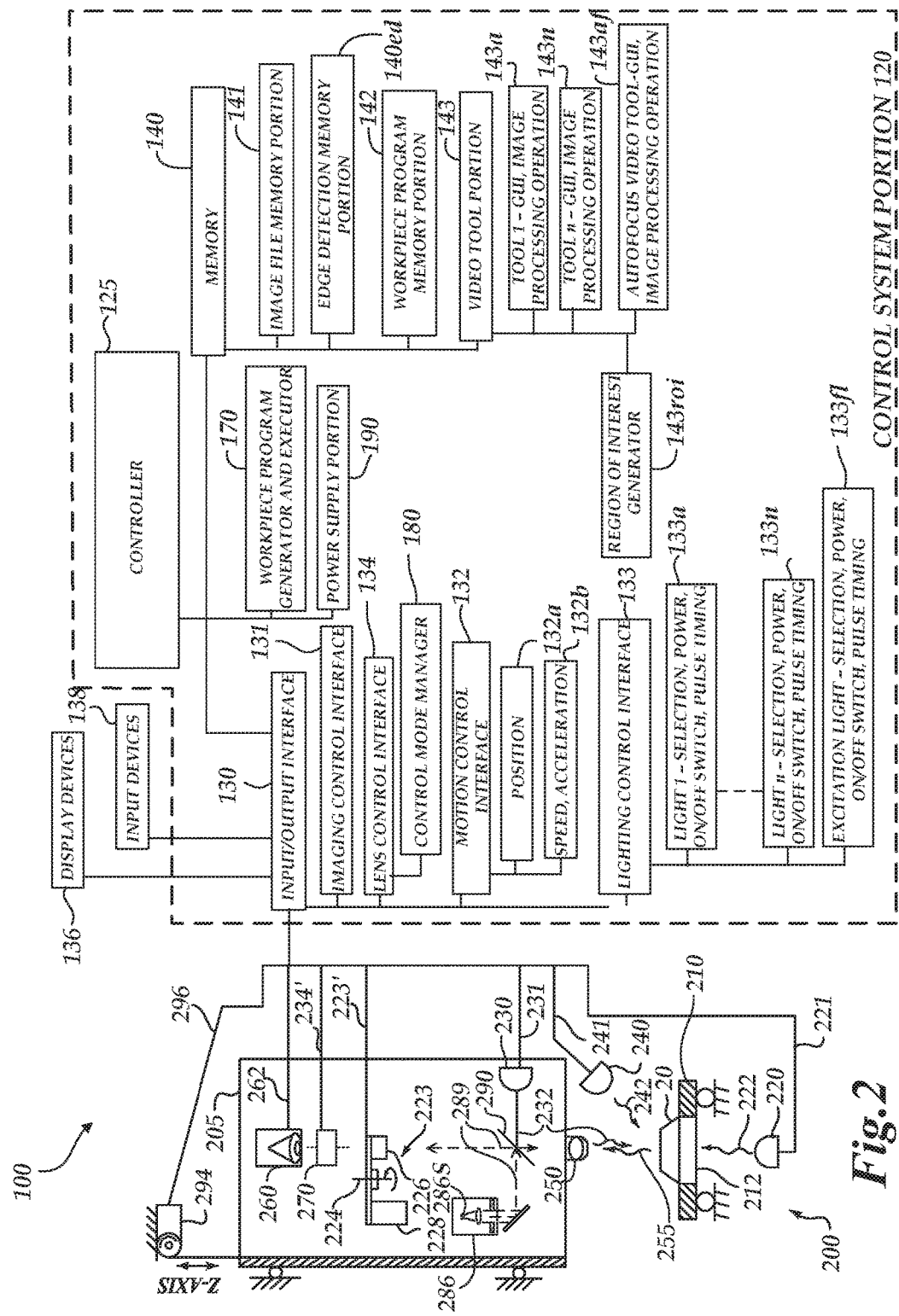
FIG. 2 is a block diagram of a control system portion and a vision components portion of a machine vision inspection system similar to that of FIG. 1 and including certain features disclosed herein.

FIG. 2 is a block diagram of a control system portion 120 and a vision components portion 200 of a machine vision inspection system 100 similar to the machine vision inspection system of FIG. 1, including features as described herein. As will be described in more detail below, the control system portion 120 is utilized to control the vision components portion 200. The vision components portion 200 includes an optical assembly portion 205, light sources 220, 230, 240, and a workpiece stage 210 having a central transparent portion 212. The workpiece stage 210 is controllably movable along x- and y-axes that lie in a plane that is generally parallel to the surface of the stage where a workpiece 20 may be positioned.

The optical assembly portion 205 includes a camera system 260, an interchangeable objective lens 250, a variable focal length (VFL) lens 270 which is a TAG lens in various exemplary implementations, and a monitoring beam generator 286 having a monitoring light source 286S. In various implementations, the optical assembly portion 205 may also include the light source 230 (e.g., a coaxial light source). In various implementations, the optical assembly portion 205 may further include a turret lens assembly 223 having lenses 226 and 228. As an alternative to the turret lens assembly, in various implementations a fixed or manually interchangeable magnification-altering lens, or a zoom lens configuration, or the like, may be included. In various implementations, the various lenses may be included as part of a variable magnification lens portion of the optical assembly portion 205. In various implementations, the interchangeable objective lens 250 may be selected from a set of fixed magnification objective lenses that are included as part of the variable magnification lens portion (e.g., a set of objective lenses corresponding to magnifications such as 0.5×, 1×, 2× or 2.5×, 5×, 10×, 20× or 25×, 50×, 100×, etc.)

The optical assembly portion 205 is controllably movable along a z-axis that is generally orthogonal to the x- and y-axes by using a controllable motor 294 that drives an actuator to move the optical assembly portion 205 along the z-axis to change the focus of the image of the workpiece 20. The controllable motor 294 is connected to an input/output interface 130 via a signal line 296. As will be described in more detail below, the VFL (TAG) lens 270 may be controlled via a signal line 234' by a lens control interface 134 to periodically modulate a focus position of the VFL lens 270. The lens control interface 134 may include a control mode manager 180 according to various principles disclosed herein, as described in greater detail below. A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the field of view of the interchangeable objective lens 250 moves between locations on a workpiece 20, and/or among a plurality of workpieces 20.

One or more of a stage light source 220, a coaxial light source 230, and a surface light source 240 (e.g., a ring light) may emit source light 222, 232, and/or 242, respectively, to illuminate the workpiece or workpieces 20. In various implementations, during a workpiece imaging mode, the coaxial light source 230 may emit source light 232 along a path including a reflecting surface 290 (e.g., a partial mirror as part of a beamsplitter). The source light 232 is reflected or transmitted as workpiece light 289, and the workpiece light used for imaging passes through the interchangeable objective lens 250, the turret lens assembly 223 and the VFL lens 270 and is gathered by the camera system 260. A workpiece image exposure which includes the image of the workpiece(s) 20, is captured by the camera system 260, and is output on a signal line 262 to the control system portion 120. The light sources 220, 230, 240 may be connected to the control system portion 120 through signal lines or busses 221, 231, 241, respectively. In various implementations, the monitoring beam generator 286 and/or the monitoring light source 286S may also be connected to the control system portion 120 through a signal line or bus. The control system portion 120 may control the turret lens assembly 223 to rotate along axis 224 to select a turret lens through a signal line or bus 223' to alter an image magnification.

Figure 3:
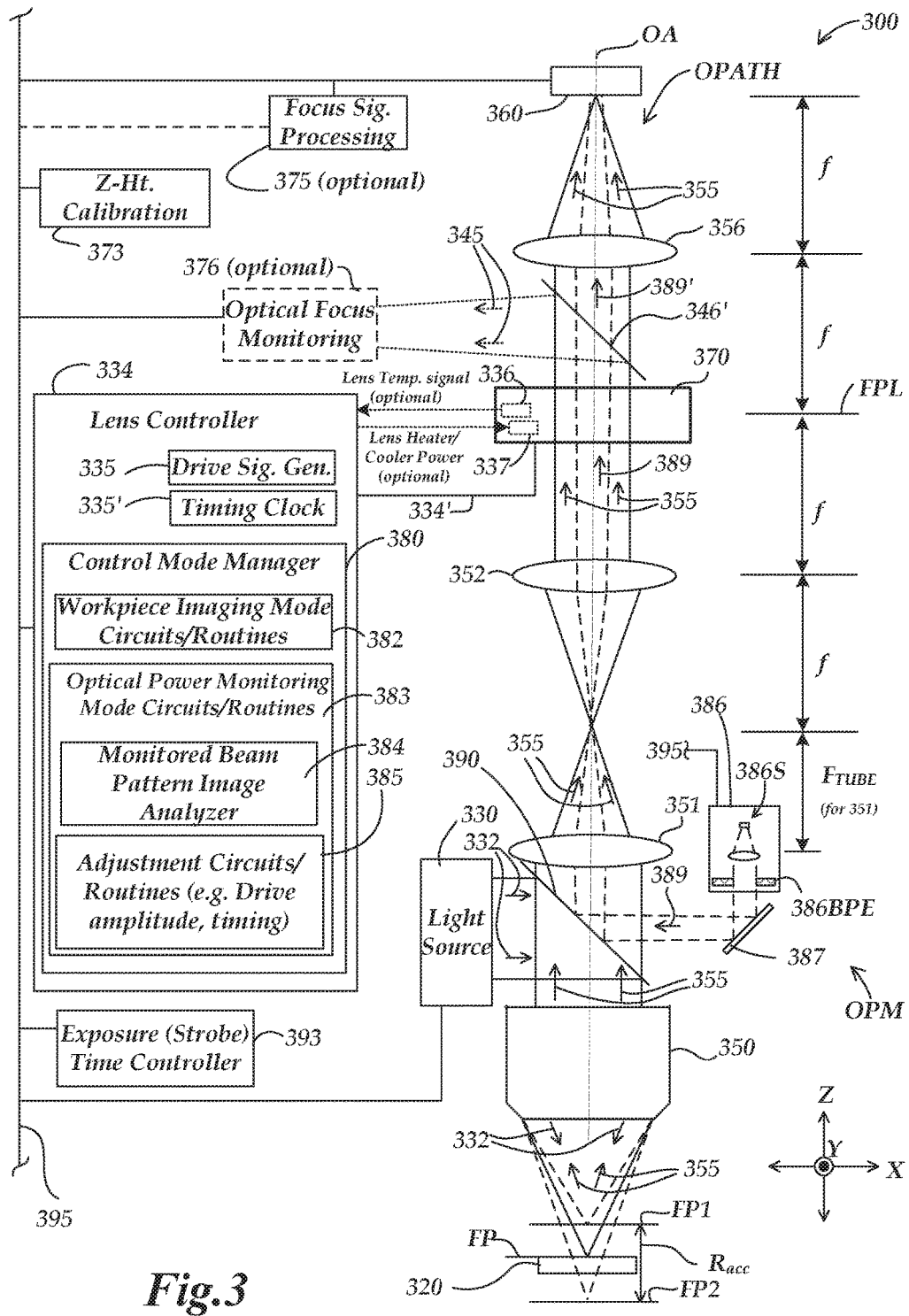
FIG. 3 is a schematic diagram of an imaging system that may be adapted to a precision non-contact metrology system such as a machine vision inspection system and operated according to the principles disclosed herein.

As shown in FIG. 2, in various exemplary implementations, the control system portion 120 includes a controller 125, the input/output interface 130, a memory 140, a workpiece program generator and executor 170, and a power supply portion 190. Each of these components, as well as the additional components described below, may be interconnected by one or more data/control busses and/or application programming interfaces, or by direct connections between the various elements. The input/output interface 130 includes an imaging control interface 131, a motion control interface 132, a lighting control interface 133, and the lens control interface 134. The lens control interface 134 may include the control mode manager 180 including circuits and/or routines for a workpiece imaging mode and an optical power monitoring mode according to principles disclosed herein, as described in greater detail below with reference to a lens controller 334 comprising circuits and/or routines as shown in FIG. 3. In some implementations, the lens control interface 134 and the lens controller 334 may be merged and/or indistinguishable.

The motion control interface 132 may include a position control element 132a, and a speed/acceleration control element 132b, although such elements may be merged and/or indistinguishable. The lighting control interface 133 may include lighting control elements 133a-133n, and 133fl that control, for example, the selection, power, on/off switch, and strobe pulse timing, if applicable, for the various corresponding light sources of the machine vision inspection system 100. The lighting control element configured to control strobe pulse timing generally corresponds to an exposure (strobe) time controller 393 as shown in FIG. 3 and as described in greater detail below.

The memory 140 may include an image file memory portion 141, an edge-detection memory portion 140ed, a workpiece program memory portion 142 that may include one or more part programs, or the like, and a video tool portion 143. The video tool portion 143 includes video tool portion 143a and other video tool portions (e.g., 143n) that determine the GUI, image-processing operation, etc., for each of the corresponding video tools, and a region of interest (ROI) generator 143roi that supports automatic, semi-automatic, and/or manual operations that define various ROIs that are operable in various video tools included in the video tool portion 143. In various implementations, various types of video tools (e.g., circle tools, arc tools, box tools, line tools, etc.) may be utilized for inspecting and/or measuring various workpiece features. Examples of the operations of such video tools for locating edge features and performing other workpiece feature inspection operations are described in more detail in certain of the previously incorporated references, as well as in U.S. Pat. No. 7,627,162, which is hereby incorporated herein by reference in its entirety.

The video tool portion 143 also includes an autofocus video tool 143af that determines the GUI, image-processing operation, etc., for focus height measurement operations. In various implementations, the autofocus video tool 143af may additionally include a high-speed focus height tool that may be utilized to measure focus heights with high speed using hardware described in FIG. 3, as described in more detail in U.S. Pat. No. 9,143,674, which is hereby incorporated herein by reference in its entirety. In various implementations, the high-speed focus height tool may be a special mode of the autofocus video tool 143af that may otherwise operate according to conventional methods for autofocus video tools, or the operations of the autofocus video tool 143af may only include those of the high-speed focus height tool.

In the context of this disclosure, and as is known by one of ordinary skill in the art, the term "video tool" generally refers to a relatively complex set of automatic or programmed operations that a machine vision user can implement through a relatively simple user interface (e.g., a graphical user interface, editable parameter windows, menus, and the like), without creating the step-by-step sequence of operations included in the video tool or resorting to a generalized text-based programming language, or the like. For example, a video tool may include a complex pre-programmed set of image-processing operations and computations that are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI) indicator through simple "handle dragging" operations using a mouse, in order to define the location parameters of a subset of an image that is to be analyzed by the image-processing operations of a particular instance of a video tool. It should be noted that the visible user interface features are sometimes referred to as the video tool, with the underlying operations being included implicitly.

One or more display devices 136 (e.g., the display 16 of FIG. 1) and one or more input devices 138 (e.g., the joystick 22, keyboard 24, and mouse 26 of FIG. 1) may be connected to the input/output interface 130. The display devices 136 and input devices 138 may be used to display a user interface that may include various graphical user interface (GUI) features that are usable to perform inspection operations, and/or to create and/or modify part programs, to view the images captured by the camera system 260, and/or to directly control the vision components portion 200. The display devices 136 may display user interface features (e.g., as associated with the video tools of the video tool portion 143, etc.)

Figure 5:
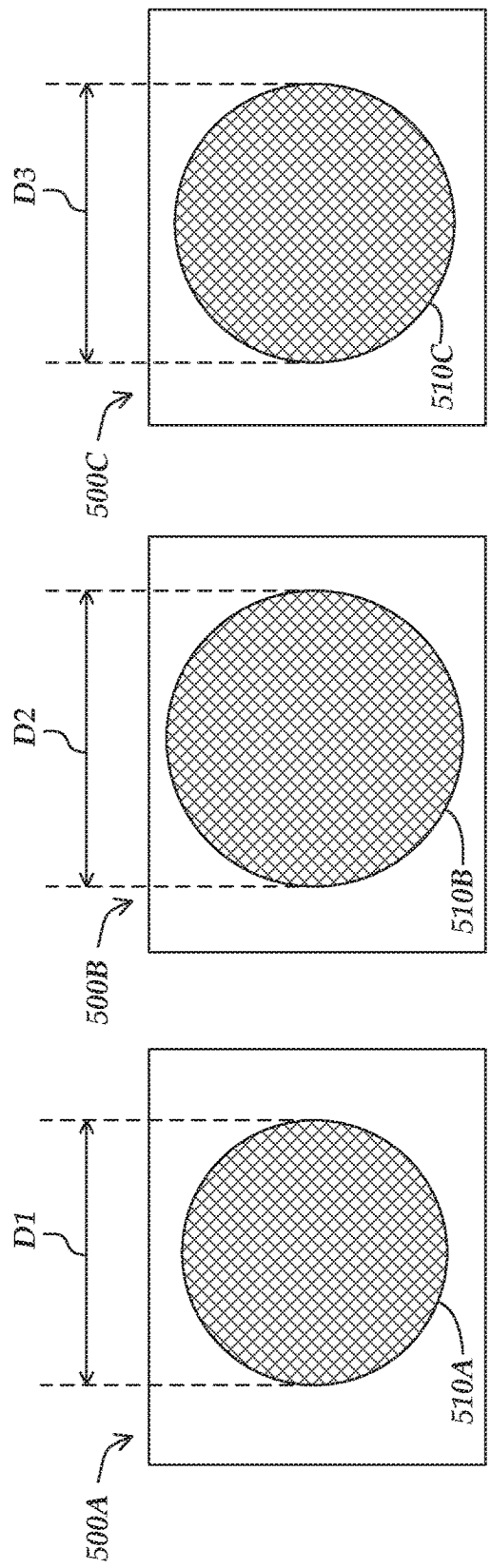
FIGS. 5A-5C are diagrams illustrating a monitored beam pattern in different monitoring image exposures as corresponding to different phase timings.

In various exemplary implementations, when a user utilizes the machine vision inspection system 100 to create a part program for the workpiece 20, the user generates part program instructions by operating the machine vision inspection system 100 in a learn mode to provide a desired image-acquisition training sequence. For example, a training sequence may comprise positioning a particular workpiece feature of a representative workpiece in the field of view (FOV), setting light levels, focusing or autofocusing, acquiring an image, and providing an inspection training sequence applied to the image (e.g., using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and cause inspection operations to automatically inspect that particular workpiece feature (that is the corresponding feature in the corresponding location) on a run mode workpiece, or workpieces, which matches the representative workpiece used when creating the part program. In various implementations, such techniques may be utilized to create a part program for inspecting (e.g., measuring dimensions of) a monitored beam pattern in monitoring image exposures (e.g., as illustrated in FIGS. 5A-5C), as will be described in more detail below.

FIG. 3 is a schematic diagram of a VFL lens system 300 (also referred to as imaging system 300) that includes a VFL lens 370 (e.g., a TAG lens) and may be adapted to a vision system and operated according to principles disclosed herein. It will be appreciated that certain numbered components 3XX of FIG. 3 may correspond to and/or have similar operations as similarly numbered components 2XX of FIG. 2, except as otherwise described herein. As will be described in more detail below, an imaging optical path OPATH comprises various optical components arranged along a path that conveys imaging light from the workpiece 320 to the camera 360. The imaging light is generally conveyed along the direction of their optical axes OA. In the implementation shown in FIG. 3, all the optical axes OA are aligned. However, this implementation is exemplary only and not limiting. More generally, the imaging optical path OPATH may include mirrors and/or other optical elements, and may take any form that is operational for imaging the workpiece 320 using a camera (e.g., the camera 360) according to known principles. In the illustrated implementation, the imaging optical path OPATH includes the VFL lens 370 (which may be included in a 4F imaging configuration) and is utilized at least in part for imaging a surface of a workpiece 320 during a workpiece imaging mode. As will be further described in more detail below, in accordance with principles disclosed herein, a monitoring light source 386S may be utilized during an optical power monitoring mode to emit monitoring light along at least a portion of the imaging optical path OPATH to pass through the VFL lens 370 to form one or more monitoring image exposures (e.g., which may be analyzed and compared to stored calibration values to enable sensing of changes in the commanded optical power of the VFL lens 370).

As shown in FIG. 3, the VFL lens system 300 includes a light source 330, an objective lens 350, a tube lens 351, a relay lens 352, a VFL (TAG) lens 370, a relay lens 356, a lens controller 334, a camera 360, a Z-height (focus distance) calibration portion 373, a focus signal processing portion 375 (optional), an optical focus monitoring portion 376 (optional), and an optical power monitoring configuration OPM including a monitoring beam generator 386. In various implementations, the various components may be interconnected by direct connections or one or more data/control busses (e.g., a system signal and control bus 395) and/or application programming interfaces, etc.

In the implementation shown in FIG. 3, the light source 330 may be a "coaxial" or other light source configured to emit the source light 332 (e.g., with strobed or continuous illumination) along a path including a reflecting surface 390 (e.g., a partial mirror as part of a beamsplitter) and through the objective lens 350 to a surface of a workpiece 320, wherein the objective lens 350 receives the workpiece light 355 that is focused at a focus position FP proximate to the workpiece 320, and outputs the workpiece light 355 to the tube lens 351. The tube lens 351 receives the workpiece light 355 and outputs it to the relay lens 352. In other implementations, analogous light sources may illuminate the field of view in a non-coaxial manner; for example a ring light source may illuminate the field of view. In various implementations, the objective lens 350 may be an interchangeable objective lens and the tube lens 351 may be included as part of a turret lens assembly (e.g., similar to the interchangeable objective lens 250 and the turret lens assembly 223 of FIG. 2). In various implementations, any of the other lenses referenced herein may be formed from or operate in conjunction with individual lenses, compound lenses, etc.

The relay lens 352 receives the workpiece light 355 and outputs it to the VFL (TAG) lens 370. The VFL (TAG) lens 370 receives the workpiece light 355 and outputs it to the relay lens 356. The relay lens 356 receives the workpiece light 355 and outputs it to the camera 360. In various implementations, the camera 360 may capture a workpiece image exposure (e.g., including an image of the workpiece 320) during an image exposure period, and may provide the corresponding image data to a control system portion. In various implementations, the camera 360 may have a pixel array greater than 1 megapixel (e.g., 1.3 megapixel, with a 1,280×1024 pixel array, with 5.3 microns per pixel).

In the example of FIG. 3, the relay lenses 352 and 356 and the VFL (TAG) lens 370 are designated as being included in a 4f optical configuration, while the relay lens 352 and the tube lens 351 are designated as being included in a Keplerian telescope configuration, and the tube lens 351 and the objective lens 350 are designated as being included in a microscope configuration. All of the illustrated configurations will be understood to be exemplary only, and not limiting with respect to the present disclosure. In various implementations, the illustrated 4f optical configuration permits placing the VFL (TAG) lens 370 (e.g., which may be a low numerical aperture (NA) device) at the Fourier plane of the objective lens 350. This configuration may maintain the telecentricity at the workpiece 320 and may minimize scale change and image distortion (e.g., including providing constant magnification for each Z-height of the workpiece 320 and/or focus position FP). The Keplerian telescope configuration (e.g., including the tube lens 351 and the relay lens 352) may be included between the microscope configuration and the 4f optical configuration, and may be configured to provide a desired size of the projection of the objective lens clear aperture at the location of the VFL (TAG) lens 370, so as to minimize image aberrations, etc.

In various implementations, the lens controller 334 may include a drive signal generator portion 335, a timing clock 335' and a control mode manager 380. The drive signal generator portion 335 may operate (e.g., in conjunction with the timing clock 335') to provide a periodic drive signal to the high speed VFL (TAG) lens 370 via a signal line 334'. In various implementations, the control mode manager 380 may include circuitry and/or routine(s) that are operable according to principles disclosed herein. In some implementations, the lens controller 334 and the control mode manager 380 may be merged and/or indistinguishable. In various implementations, the VFL lens system (or imaging system) 300 may comprise a control system (e.g., the control system portion 120 of FIG. 2) that is configurable to operate in conjunction with the lens controller 334 to control the VFL (TAG) lens 370 via the signal line 334', by driving the VFL (TAG) lens 370 to periodically modulate its focus position.

In various implementations, the control mode manager 380 may generally perform various functions (e.g., such as operating as a sequence manager in the lens controller 334 for different modes of operation, etc.) The control mode manager 380 includes a workpiece imaging mode circuits/routines portion 382 and an optical power monitoring mode circuits/routines portion 383. In various implementations, the workpiece imaging mode circuits/routines portion 382 performs a workpiece imaging mode (i.e., also referenced herein as a standard imaging mode) which includes performing standard workpiece imaging operations for the optical system, as are known in the art and as are described in the incorporated references. As will be described in more detail below, in various implementations the optical power monitoring mode circuits/routines portion 383 may perform an optical power monitoring mode in accordance with principles disclosed herein. In various implementations, the optical power monitoring mode may be performed on an on-demand basis (e.g., in response to a user selection in a user interface, or when a particular condition is detected, etc.), or may be performed periodically (once every 10 seconds, once per day, etc.) In various implementations, the control mode manager 380 may operate such that the optical power monitoring mode does not overlap with the workpiece imaging mode, although any adjustments to the system (e.g., to adjust the operation of the VFL lens 370) determined during the optical power monitoring mode will continue to be applied and utilized during subsequent execution of the workpiece monitoring mode.

The optical power monitoring mode circuits/routines portion 383 includes a monitored beam pattern image analyzer portion 384 and an adjustment circuits/routines portion 385. In various implementations, the monitored beam pattern image analyzer portion 384 may perform functions such as inputting monitoring image exposures and calling certain video tools (e.g., an edge detection video tool such as a circle video tool, etc.) or other size analyzer (e.g., to determine one or more dimensions of a monitored beam pattern in the monitoring image exposures, etc.) In various implementations, the adjustment circuits/routines portion 385 may input the dimensional results/values from the monitored beam pattern image analyzer portion 384, and may compare the results/values to calibration values, in order to determine whether adjustments (e.g., to the operation of the VFL lens) need to be made. As will be described in more detail below, in various implementations adjustments may include adjusting an amplitude A for driving the VFL lens 370 (e.g., for adjusting the Z range), a phase timing adjustment (e.g., for adjusting a Z offset), a temperature adjustment, etc. In various implementations, such adjustments may be implemented through changes to the control signals of the drive signal generator 335, timing clock 335', and/or lens heater/cooler 337, etc. As will be described in more detail below, in various implementations the optical power monitoring mode circuits/routines portion 383 may in some instances repeatedly perform operations to iteratively analyze and adjust the system until the optical power of the VFL lens is at least approximately at desired levels (e.g., corresponding to stored calibration values).

As shown in FIG. 3, in various implementations the imaging system 300 may optionally include the lens heater/cooler 337 associated with the VFL lens 370. The lens heater/cooler 337 may be configured to input an amount of heat energy into the VFL lens 370 and/or perform cooling functions to facilitate heating and/or cooling of the VFL lens 370 according to some implementations and/or operating conditions. In addition, in various implementations a VFL lens monitoring signal may be provided by a temperature sensor 336 associated with the VFL lens 370 to monitor an operating temperature of the VFL lens 370.

As will be described in more detail below, during an optical power monitoring mode, monitoring image exposures may be provided through operation of the camera 360 in combination with the optical power monitoring configuration OPM. In various implementations, the optical power monitoring configuration OPM includes the monitoring beam generator 386 comprising the monitoring light source 386S and a beam pattern element 386BPE (e.g., an aperture element) that inputs light from the monitoring light source 386S and outputs a monitored beam pattern (e.g., as will be described in more detail below with respect to FIGS. 5A-5C). In one specific example implementation, the monitoring light source 386S may be an LED that functions as a point source emitting light with a width of approximately 150 micrometers or less, and a 90 degree emission. In various implementations, the monitoring light source 386S may be located, and/or the optical power monitoring configuration OPM may be located, so as to direct the monitoring light from a Fourier plane of the microscope configuration of the objective lens 350 and the tube lens 351. In various implementations, the optical power monitoring configuration OPM transmits the monitored beam pattern along at least a portion of the imaging optical path OPATH to travel through the VFL lens 370 to the camera 360 during the optical power monitoring mode. As will be described in more detail below with respect to FIGS. 5A-5C, the camera 360 provides monitoring image exposures 500A-500C including the monitored beam pattern during corresponding phase timings of the periodic modulation of the VFL lens 370 during the optical power monitoring mode. A dimension of the monitored beam pattern in the monitoring image exposures 500A-500C is related to an optical power of the VFL lens 370 during the corresponding phase timings.

In various implementations, the beam pattern element 386BPE is an aperture element including an aperture (i.e., that is located between the monitoring light source 386S and a reflecting surface 387 which directs the light 389 of the monitored beam pattern toward the reflecting surface 390). In various implementations, it may be desirable for the aperture to yield a small beam divergence (i.e., as opposed to no beam divergence) so as to yield at the camera 360 a large monitored beam pattern diameter throughout the optical scan range of the VFL lens, as will be described in more detail below with respect to FIGS. 5A-5C. The reflecting surface 390 directs the light 389 of the monitored beam pattern along the imaging optical path OPATH, which passes through the VFL lens 370 and emerges as light 389' which forms the image of the monitored beam pattern in the monitoring image exposure that is produced by the camera 360 during the optical power monitoring mode. As described above, during the workpiece imaging mode, the reflecting surface 390 directs imaging source light 332 from the workpiece imaging light source 330 toward the surface of the workpiece 320 and transmits the workpiece light 355 arising from the surface of the workpiece 320.

The monitoring beam generator 386 is connected to the system signal and control bus 395 (e.g., for controlling the timing of the monitoring light source 386S, etc.) In various implementations, the monitoring light source 386S may be controlled by the exposure strobe time controller 393, which may provide strobe timing for both the monitoring light source 386S and the workpiece imaging light source 330. In various implementations, the monitoring light source 386 may include a lens that provides the desired divergence, or near collimation, for the light that passes through the beam pattern element 386BPE and results in the monitored beam pattern. It will be appreciated that in other implementations, other locations and/or configurations of the components of the optical power monitoring configuration OPM may be utilized. For example, in one alternative implementation, the monitoring beam generator 386 may be located on the same side of the reflecting surface 390 as the light source 330, with corresponding transmissive and/or reflective properties of the reflecting surface 390 and/or additional reflective surfaces utilized for directing the monitoring light 389 along the imaging optical path OPATH.

In various implementations, a reflecting surface 387 of the optical power monitoring configuration OPM may be a dichroic reflecting surface that reflects the light 389 of the monitored beam pattern from the beam pattern element 386BPE toward the reflecting surface 390. As noted above, the reflecting surface 390 directs the light 389 of the monitored beam pattern along at least a portion of the imaging optical path OPATH to travel through the VFL lens 370 and to emerge as light 389' which is received by the camera 360 during the optical power monitoring mode. In various implementations, the light 389 and 389' of the monitored beam pattern has a wavelength that is different than a wavelength of the imaging source light 332, and the dichroic reflecting surface 387 primarily transmits rather than reflects any of the imaging source light 332 that reaches the dichroic reflecting surface 387. In certain configurations, the characteristic of the reflecting surface 387 being dichroic, and thus transmitting rather than reflecting the imaging source light 332, prevents unwanted source light 332 from being directed back through the imaging optical path OPATH and appearing in a workpiece image exposure (e.g., as a ghost image portion or other undesirable image contribution in the workpiece image exposure).

In various implementations, the light 389 of the monitored beam pattern has a pattern and beam divergence that is determined by the monitoring beam generator 386. The VFL lens 370 receives the light 389 of the monitored beam pattern and outputs the light 389' of the monitored beam pattern, for which the divergence and pattern size of the light 389' are periodically altered by the periodic optical power variation associated with the operation of the VFL lens 370. In various implementations, the light 389' of the monitored beam pattern underfills the field of view of the camera 360 during all phase timings of the periodic modulation of the VFL lens 370 during the optical power monitoring mode. In various implementations, the light 389' of the monitored beam pattern may be at least approximately collimated at the camera 360. As will be described in more detail below, in various implementations dimensions (e.g., diameters) of the monitored beam pattern in first and second monitoring image exposures (e.g., corresponding to 0 and 180 degree phase timings) are measured (e.g., utilizing an edge detection video tool, such as a circle video tool). The measured dimensions are used to determine a measured difference value (e.g., a difference between the diameters) that is compared to a calibration value, and an adjustment (e.g., to the operation of the VFL lens 370) is made (e.g., by the lens controller 334) based at least in part on the comparison of the measured difference value to the calibration value.

In various applications, and particularly for some metrology applications, it is advantageous if the magnification of the VFL lens system 300 is constant (or at least stable and known) for all optical powers. It is possible to determine what a diameter of the monitored beam pattern may be for various optical powers when the VFL system is configured and/or carefully adjusted for constant magnification. For example, the VFL lens system 300 may be adjusted for constant magnification at various optical powers according to known methods, and then the monitored beam pattern may be measured at various optical powers on that system to establish a reference curve for the dimension of monitored beam pattern as a function of optical power (or vice versa) for that system and substantially similar systems. Such a reference curve may be determined by experiment, analysis and/or simulation. Conversely, when a system exhibits deviations from such a reference curve, those deviations are indicative of non-constant magnification due to improper optical alignment, or thermal distortion, or the like. The indicated magnification error component may be determined and/or eliminated. For example, in some implementations, various dimensions such as the diameter of the monitored beam pattern in at least first and second monitoring image exposures may be measured. Such measurements may include a component related to an optical magnification of the VFL lens 370 during the phase timing or optical power corresponding to the at least first and second monitoring image exposures, as outlined above. It may then be determined whether the measurement corresponds to a constant magnification reference curve, or whether they exhibit deviations from the reference curve. If a deviation from the reference curve is indicated, at least one of a stored optical magnification value or a physical component location that affects the optical magnification of the VFL lens system 300 may be adjusted based on an optical magnification (e.g. a deviating optical magnification) determined based, at least in part, on the diameter of the monitored beam pattern in the first and second monitoring image exposures. In some implementations, it may be advantageous to simply correct a measurement by compensating a stored optical magnification value based on an optical magnification deviation determined as outlined above. In other implementations, it may be advantageous to actually adjust the alignment of the components of the VFL lens system 300 to establish or reestablish constant magnification at all optical powers.

With respect to the general operations of the VFL lens 370, in various implementations as described above, the lens controller 334 may rapidly adjust or modulate the focus position periodically, to achieve a high-speed VFL lens capable of a periodic modulation (i.e., at a VFL lens resonant frequency) of 250 kHz, or 70 kHz, or 30 kHz, or the like. As shown in FIG. 3, by using the periodic modulation of a signal to drive the VFL lens 370, the focus position FP of the imaging system 300 may be (rapidly) moved within a range $R_{acc}$ (e.g., an autofocus search range) bound by a focus position FP1 and a focus position FP2 (e.g., which in various implementation may at least approximately correspond to phase timings of 0 degrees and 180 degrees, as will be described in more detail below).

In one implementation, the optional focus signal processing portion 375 (optional) may input data from the camera 360 and may provide data or signals (focus monitoring signals, or FMSs) that are utilized to determine when an imaged surface region (e.g., of the workpiece 320) is at a focus position. For example, a group of images acquired by the camera 360 at different Z heights (e.g., an image stack), may be analyzed using a known "maximum contrast" analysis to determine when an imaged surface region of the workpiece 320 is at a focus position. In another implementation, the optical focus monitoring portion 376 (optional) may provide a focus monitoring signal (FMS), for example a signal from a photodetector, derived from image light 345 that passes through the VFL (TAG) lens 370 and is deflected from a beamsplitter 346' to the optical focus monitoring portion 376. In one implementation, the optical focus monitoring portion 376 may comprise a confocal optical detector configuration. However, more generally any other suitable known focus detection configuration may be used.

In any case, the focus signal processing portion 375 or the optical focus monitoring portion 376 may input image light during the periodic modulation of the focus position (sweeping of multiple focus positions) of the VFL (TAG) lens 370 and output a corresponding focus monitoring signal (FMS) to the Z-height (focus distance) calibration portion 373. The Z-height calibration portion 373 may provide a Z-height (focus distance) versus FMS value characterization that relates respective Z-heights (focus distances) to respective FMS values indicative of images in focus. The Z-height calibration portion 373 may further provide Z-height (focus distance) calibration data that relates respective Z-heights (focus distances) to respective phase timings within a period of a standard imaging resonant frequency of the VFL lens 370, wherein the calibration data corresponds to operating the VFL lens 370 according to the standard imaging drive control configuration.

Because the phase timings within a period of the VFL lens's standard imaging resonant frequency can be correlated to the FMS values or timings, the Z-height calibration data that relates respective Z-heights to respective phase timings can be derived from the Z-height versus FMS value characterization received from the focus signal processing portion 375 or the optical focus monitoring portion 376. Alternatively, the Z-height calibration data may be otherwise defined and stored in the Z-height calibration portion 373. Generally speaking, the Z-height calibration portion 373 comprises recorded Z-height calibration data. As such, its representation in FIG. 3 as a separate element is intended to be a schematic representation only, and not limiting. In various implementations, the associated recorded Z-height calibration data may be merged with and/or indistinguishable from the lens controller 334, the focus signal processing portion 375, the optical focus monitoring portion 376, or a host computer system connected to the system signal and control bus 395, etc. As described above, certain types of changes (e.g., ambient temperature changes, mechanical distortions, etc.) may slightly affect the operating characteristics of the VFL lens and/or otherwise affect the system (e.g., causing changes to the Z range, Z offset, etc.), which may correspondingly affect the accuracy of measurements/values determined utilizing the Z-height calibration data. To address such issues, in accordance with principles disclosed herein, the optical power of the VFL lens 370 may be monitored and corresponding adjustments may be made to the system to cause the optical power to more closely conform to the operating characteristics used during calibration, so as to improve the accuracy of measurements/values determined utilizing the Z-height calibration data.

In various implementations, the exposure (strobe) time controller 393 controls an image exposure time of the imaging system 300 (e.g., relative to a phase timing of the periodically modulated focus position) and may be merged with or indistinguishable from the camera 360. Specifically, during a workpiece imaging mode, the exposure (strobe) time controller 393 (e.g., using the Z-height calibration data available in the Z-height calibration portion 373), may control the light source 330 including a strobe light source to strobe at a respective controlled time. For example, the exposure (strobe) time controller 393 may control the strobe light source to strobe at a respective phase timing within a period of a standard imaging resonant frequency of the VFL lens 370, so as to acquire an image in best focus within the sweeping (periodic modulation) range of the VFL lens 370. In other implementations, the exposure time controller 393 may control a fast electronic camera shutter of the camera 360 to acquire an image signal at a respective controlled time. For example, the exposure time controller 393 may control the camera shutter at a respective phase timing within the period of the standard imaging resonant frequency of the VFL lens 370 so as to acquire an image in best focus within the sweeping (periodic modulation) range of the VFL lens 370.

Generally, during a workpiece imaging mode, the exposure time controller 393 controls acquisition of image data by controlling an image exposure period during which the camera 360 captures a workpiece image exposure of the workpiece 320. For example, during the workpiece imaging mode, image data of the workpiece 320 may be acquired and displayed in a user interface of the imaging system 300 (see FIG. 2, display devices 136). As will be described in more detail below, in various implementations the exposure time controller 393 may similarly control acquisition of image data by controlling an image exposure period during which the camera 360 captures monitoring image exposures. As will be described in more detail below with respect to FIGS. 5A-5C, in certain specific example implementations, such monitoring image exposures may correspond to specified phase timings, such as phase timings of 0 degrees and 180 degrees (i.e., for end of range images) and a phase timing of 90 degrees (i.e., for a mid-range image approximately corresponding to a best-focus Z position). In various implementations, image data may be acquired by the camera 360 during the optical power monitoring mode and may in some instances be displayed in a user interface of the imaging system 300 (e.g., see FIG. 2, display devices 136), or alternatively may not be outputted by the imaging system 300 (e.g., utilized primarily internally for determining and making adjustments, etc.)

Figure 4:
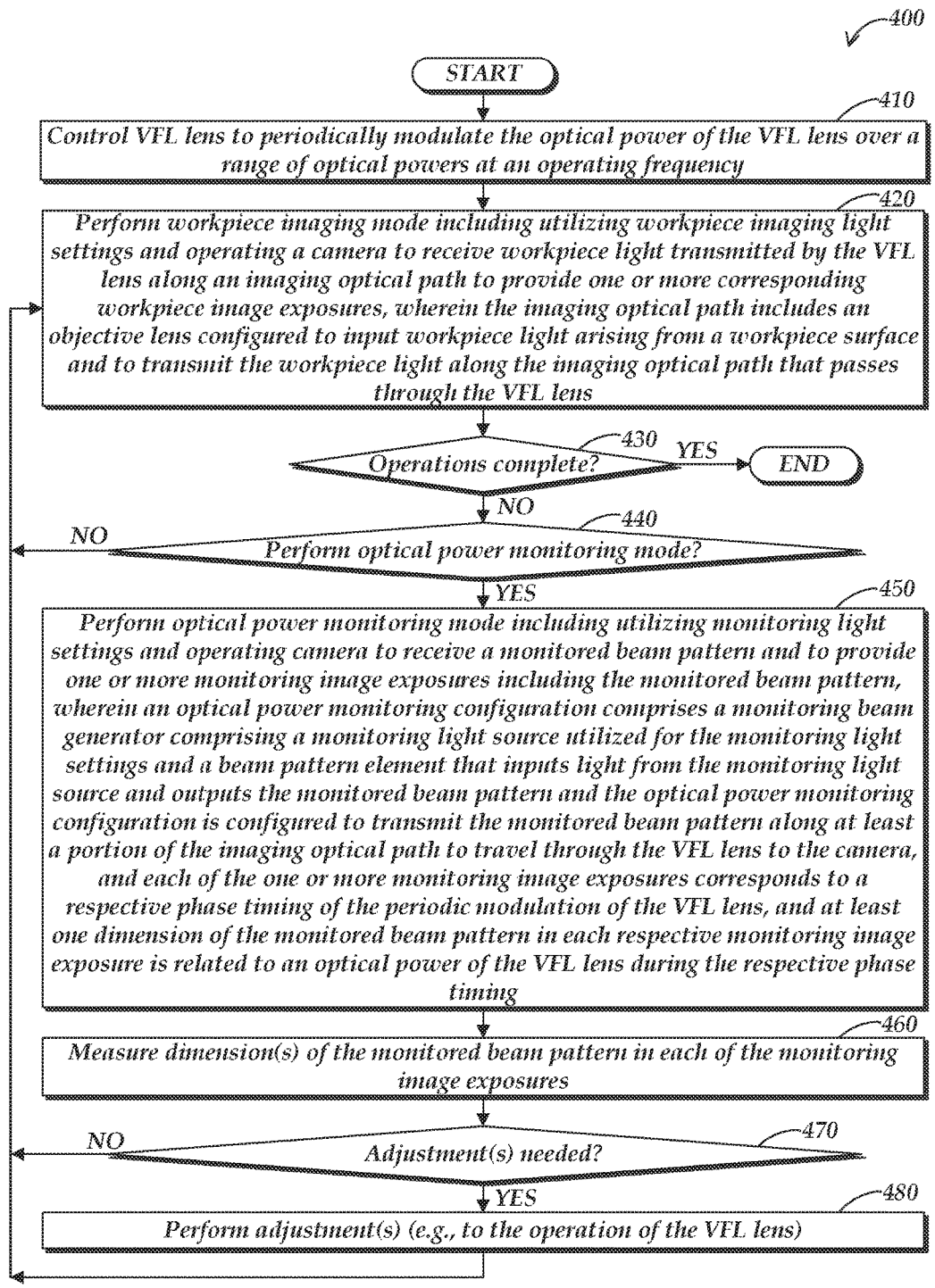
FIG. 4 is a flow diagram illustrating an exemplary implementation of a routine for operating an imaging system including a VFL lens.

FIG. 4 is a flow diagram illustrating an exemplary implementation of a routine 400 for operating an imaging system including a VFL lens, in accordance with principles disclosed herein. At block 410, the VFL lens is controlled so as to periodically modulate the optical power of the VFL lens over a range of optical powers at an operating frequency. At block 420, a workpiece imaging mode is initiated and performed, wherein the workpiece imaging mode includes utilizing workpiece imaging light settings and operating a camera to receive workpiece light transmitted by the VFL lens along an imaging optical path to provide one or more corresponding workpiece image exposures. In various implementations, the imaging optical path includes an objective lens that is configured to input workpiece light arising from a workpiece surface and to transmit the workpiece light along the imaging optical path that passes through the VFL lens.

At decision block 430, a determination is made as to whether operations of the system are complete (e.g., if no more imaging operations are to be performed at the present time). If operations of the system are complete, the routine ends, otherwise the routine continues to decision block 440 where a determination is made as to whether an optical power monitoring mode is to be performed. For example, in various implementations an optical power monitoring mode may be performed at specified time intervals, or upon request of a user, etc. If an optical power monitoring mode is to be performed, the routine continues to block 450, as will be described in more detail below. If an optical power monitoring mode is not to be performed, the routine returns to block 420, where the workpiece imaging mode is continued.

At block 450, an optical power monitoring mode is initiated and performed, wherein the optical power monitor mode includes utilizing monitoring light settings and operating the camera to receive a monitored beam pattern and to provide one or more monitoring image exposures including the monitored beam pattern (e.g., as will be described in more detail below with respect to FIGS. 5A-5C). In various implementations, an optical power monitoring configuration comprises a monitoring beam generator comprising a monitoring light source utilized for the monitoring light settings and a beam pattern element that inputs light from the monitoring light source and outputs the monitored beam pattern. The optical power monitoring configuration may be configured to transmit the monitored beam pattern along at least a portion of the imaging optical path to travel through the VFL lens to the camera during the optical power monitoring mode. Each of the one or more monitoring image exposures may correspond to a respective phase timing of the periodic modulation of the VFL lens. At least one dimension of the monitored beam pattern in each respective monitoring image exposure may be related to an optical power of the VFL lens during the respective phase timing.

At block 460, the at least one dimension of the monitored beam pattern is measured in each of the monitoring image exposures. At decision block 470, a determination is made as to whether adjustments (e.g., to the operation of the VFL lens) are needed based at least in part on the at least one measured dimension of the monitored beam pattern in each of the monitoring image exposures. For example, as will be described in more detail below, the measured dimension may be utilized to determine a measured value which may be compared to a calibration value to determine if an adjustment is needed. If an adjustment is needed, the routine proceeds to block 480, as will be described in more detail below. If no adjustment is needed, the routine returns to block 420 to continue the performance of the workpiece imaging mode.

At block 480, at least one adjustment (e.g., to the operation of the VFL lens) is performed. As noted above, such adjustment may, in various specific example implementations, include adjusting an amplitude A for driving the VFL lens 370 (e.g., for adjusting the Z range), a phase timing adjustment (e.g., for adjusting a Z offset), a temperature adjustment, etc. In various implementations, as part of the optical power monitoring mode, such adjustments may be performed iteratively, including repeating blocks 450-470 for analyzing and adjusting until no further adjustment is needed for the measured values to at least approximately correspond to the calibration values. Once the adjustment process is complete, the routine returns to block 420 to utilize the system as adjusted to perform the workpiece imaging mode.

It will be appreciated that utilization of an optical power monitoring mode such as that disclosed herein may have various advantages. For example, for points from focus operations and other types of pulsed VFL lens modes (e.g., multi-plane, etc.) it may be desirable to ensure optical accuracy for the Z positioning in such systems to less than 1% errors. As noted above, in various implementations errors may occur due to the Z range shifting (e.g., due to ambient temperature changes, drift in assembly performance, etc.) For a VFL lens power specification of +/−1 diopter, in one specific example implementation it may be desirable to be able to detect and adjust for a 1% shift, which may correspond to an ability to be able to measure a change of 0.01 diopter. More specifically for a +/−1 diopter set point, it may be desirable to be able to measure a change to 0.99 or 1.01 diopter. Similar reasoning applies to a negative power set point. After measuring such changes, it may be desirable to be able to estimate an amount of adjustment (e.g., compensation) that is needed for the system (e.g., for adjusting the Vp-p bias to PZT for the operation of the VFL lens, etc.) In various implementations, it may be desirable to be able to make such determinations without influence from a given workpiece that is being measured. With respect to such desired levels of accuracy, a specific example configuration that is able to achieve such levels will be described in more detail below with respect to FIGS. 5A-5C.

In addition to Z range considerations, issues related to the Z offset (e.g., as related to a best focus position of the optical power monitoring configuration OPM) may also occur (e.g., due to ambient temperature changes, etc.) In various implementations, a best focus position of the optical power monitoring configuration OPM may generally correspond to a 90 degree phase timing, as will be described in more detail below with respect to FIGS. 5-7. With regard to such issues, in one specific example implementation it may be desirable to be able to track the best focus position to less than or equal to 0.25 depth of field (DOF). After measuring such changes, it may be desirable to be able to estimate an amount of adjustment (e.g., compensation) that is needed for the system (e.g., for adjusting an illumination strobe timing, etc.) In various implementations, it may be desirable to be able to make such determinations without influence from a given workpiece that is being measured. With respect to such desired levels of accuracy, a specific example configuration that is able to achieve such levels will be described in more detail below with respect to FIGS. 5A-5C.

FIGS. 5A-5C are diagrams illustrating dimensions D1-D3 of a monitored beam pattern in different monitoring image exposures 500A-500C as corresponding to different phase timings PH1-PH3, respectively. With respect to FIG. 5A, the corresponding phase timing PH1=0 degrees, for FIG. 5B the corresponding phase timing PH2=180 degrees, and for FIG. 5C the corresponding phase timing PH3=90 degrees. In this example implementation, the phase timings PH1 and PH2 are, thus, approximately 180 degrees apart (e.g., as corresponding to respective opposite end of range positions), and the phase timing PH3 is approximately halfway between the first and second phase timings PH1 and PH2 at approximately 90 degrees different than each of the first and second phase timings PH1 and PH2 (e.g., as corresponding at least approximately to a best focus position). In the examples of FIGS. 5A-5C, the dimensions D1-D3 correspond to the diameters of the monitored beam pattern images 510A-510C in each of the monitoring image exposures 500A-500C, respectively. As will be described in more detail below with respect to FIG. 6, in various implementations the dimensions D1-D3 may be measured (e.g., utilizing one or more edge detection video tools, such as a circle video tool), for which comparisons may be made to calibration values to determine if adjustments need to be made (e.g., to the operation of the VFL lens 370, etc.)

In various implementations, the phase timing PH3=90 degrees may be intended to at least approximately correspond to a best focus timing, and the phase timings PH1=0 degrees and PH2=180 degrees may be intended to at least approximately correspond to end of range timings for which a difference between the two may be indicative of a current Z scan range with respect to the periodic modulation of the VFL lens. In various implementations, certain types of changes (e.g., ambient temperature changes, drift in assembly performance, etc.) may cause changes to the Z scan range and/or best focus timing, for which the ability to monitor the system with respect to such changes and make adjustments (e.g., to return the system to desired operating levels) may be desirable. In this regard, by determining calibrated values corresponding to dimensions D1*, D2* and D3* (i.e., as described in more detail below with respect to FIG. 7), and comparing the calibrated values to currently measured values for the dimensions D1, D2 and D3 (i.e., as described in more detail below with respect to FIG. 6), changes may be detected and adjustments may be made to return/adjust the system to desired operating levels.

With respect to the sizes of the monitored beam patterns 510A-510C in the monitoring image exposures 500A-500C, as noted above in various implementations, the beam pattern element 386BPE of FIG. 3 is an aperture element including an aperture. In various implementations, the size of the aperture may be selected according to a desired size of the monitored beam pattern images 510A-510C in the monitoring image exposures 500A-500C that are produced by the camera 360, which may also correspond to a sensitivity to an optical power shift of the VFL lens. For example, in various implementations it may be desirable to increase the size of the aperture of the beam pattern element 386BPE to produce a size of the monitored beam pattern images 510A-510C that is approximately as large as possible while still underfilling the field of view of the camera 360 during all phase timings of the periodic modulation of the VFL lens (i.e., with no clipping of any portion of the monitored beam pattern images 510A-510C in any of the monitoring image exposures 500A-500C).

In one specific example implementation, in a system with an operating setpoint for driving the VFL lens of 70 kHz and a total power of +/−1 diopter, an aperture size of approximately 10.0 mm may correspond to measured dimensions (e.g., diameters) of D1=4.322 mm and D2=4.808 mm, with a difference value of D12=0.486 mm=91.4 pixels, with a corresponding slope of approximately 45.72 pixels/diopter. In such a system, a desired ability to be able to detect a 0.01 diopter change corresponds to a need to able to detect a change of approximately 0.46 pixels, which is within the sensitivity range of a system for which edge detection tools (e.g., a circle tool utilizing many scan lines) can perform edge detection (i.e., for determining the circle diameter) to a high resolution (e.g., to a 0.05 pixel resolution). In further respect to such an example system, the configuration may also correspond to a measured dimension (e.g., diameter) of D3=4.578 mm, for which a ⅕ depth of field (DOF) shift may correspond to approximately 0.6 pixels. In such a system, a desired ability to detect a ¼ DOF change (i.e., which would correspondingly be larger than the 0.6 pixels of the ⅕ DOF shift), is within the accuracy range of a system as noted above that can perform edge detection to a high resolution (e.g., to a 0.05 pixel resolution).

Figure 6:
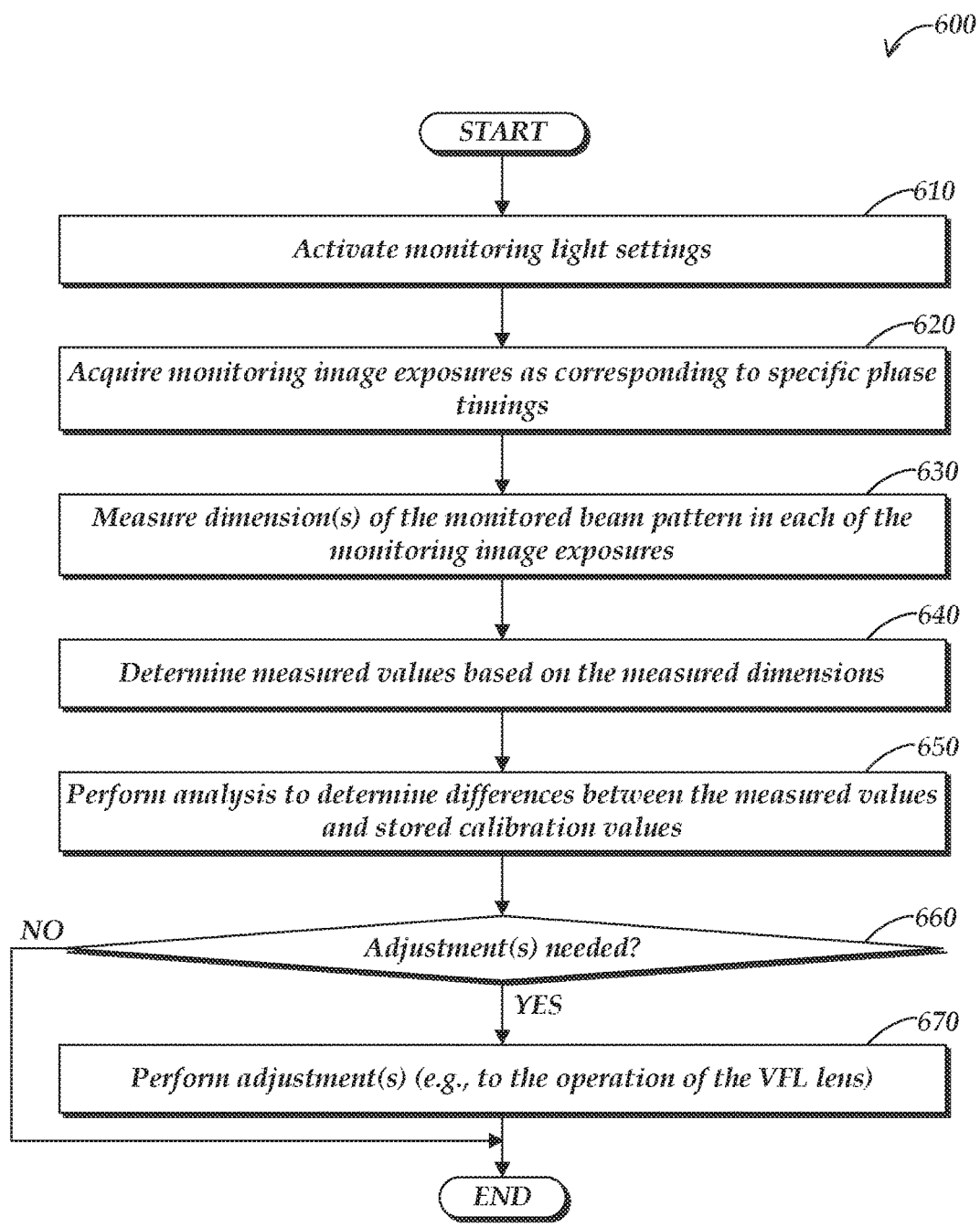
FIG. 6 is a flow diagram illustrating an exemplary implementation of a routine for analyzing monitoring image exposures such as those of FIGS. 5A-5C as compared to stored calibration values.

FIG. 6 is a flow diagram illustrating an exemplary implementation of a routine 600 for analyzing monitoring image exposures such as those of FIGS. 5A-5C as compared to stored calibration values. In various implementations, the routine 600 may correspond to a specific example implementation of the operations of blocks 450-480 of FIG. 4. As shown in FIG. 6, at block 610, monitoring light settings are activated. In one implementation, the monitoring light settings may include, for example, turning on a monitoring light source (e.g., light source 386S), and turning off a workpiece imaging light source (e.g., light source 330). In various implementations, rather than utilizing separate light sources, a single light source may provide the light that is utilized during both the workpiece imaging mode and the optical power monitoring mode.

At block 620, monitoring image exposures are acquired as corresponding to specific phase timings. For example, as described above with respect to FIG. 5A-5C, in one specific example implementation three monitoring image exposures 500A-500C may be acquired as corresponding to phase timings of 0 degrees, 180 degrees, and 90 degrees, respectively. In various implementations, each of the monitoring image exposures (e.g., monitoring image exposures 500A-500C) may include a respective monitored beam pattern image (e.g., monitored beam pattern images 510A-510C), and may in various implementations each be acquired with a light source (e.g., light source 386S) timing pulse of a specified duration (e.g., approximately 50 nanoseconds), as may be controlled by an exposure strobe time controller (e.g., exposure time controller 393).

At block 630, dimensions of the monitored beam pattern are measured in each of the monitoring image exposures. For example, as described above with respect to FIGS. 5A-5C, the dimensions D1-D3 may correspond to the diameters of the monitored beam pattern images 510A-510C, which in various implementations may be measured utilizing one or more edge detection video tools, etc. For example, in one specific example implementation, a circle video tool may be utilized that operates by having an inner circle and an outer circle define a region of interest that includes the circumference of the respective monitored beam pattern image 510A-510C. Multiple radially oriented scan lines may extend between the inner and outer circles and may be utilized (e.g., utilizing standard edge detection contrast techniques) to determine the locations of the edge points along the edge of the circumference of the respective monitored beam pattern image 510A-510C. Such edge point locations may be determined with an accuracy in certain implementations to approximately ¹⁄₂₀th of a pixel (i.e., 0.05th of a pixel), from which corresponding diameters (i.e., dimensions D1-D3) of the monitored beam pattern images 510A-510C may be determined. In various implementations, an average diameter may be determined for each of the respective monitored beam pattern images 510A-510C based on multiple edge points on opposite sides of the circumference that are determined utilizing the circle video tool. In some implementations, it is possible to detect (image) edge points along "scanlines" with subpixel accuracy, using known methods. Then a circle may be fit to hundreds of such edge points, which may provide diameter measurement repeatability or resolution on the order of ¹⁄₂₀ pixel, as outlined above.

At block 640, measured values are determined based on the measured dimensions. For example, a measured value D12 may be determined in accordance with the following equation:

$$D12 = (D1 - D2) \qquad \text{(Eq. 1)}$$

A measured value D3 may simply correspond to the measured dimension D3. At block 650, analysis is performed to determine differences between the measured values and stored calibration values. For example, the measured value D12 may be compared to a calibration value D12* for a +/−1 diopter configuration, as will be described in more detail below with respect to FIG. 7. At decision block 660, a determination is made as to whether adjustments (e.g., to the operation of the VFL lens) are needed based at least in part on the measured dimensions/values of the monitored beam pattern in each of the monitoring image exposures. If an adjustment is needed, the routine proceeds to block 670, as will be described in more detail below. If no adjustment is needed, the routine ends.

At block 670, adjustments are performed based on the differences between the measured values and the calibration values. For example, one type of adjustment that may be made is to iterate the amplitude A for the VFL lens up and/or down until the measured value D12 is at least approximately equal to the calibration value D12* in order to yield a more constant Z scan range for a +/−1 diopter configuration. As another example, within a certain tolerance span, the phase of the exposure time controller 393 (i.e., which may control both the workpiece light source 330 and the monitoring light source 386S) may be adjusted to maintain a best-focus Z position (e.g., by adjusting the phase so that the measured value D3 is made to be approximately equal to the calibration value D3*). As another example, the VFL lens temperature may be adjusted for heating up or cooling down (e.g., utilizing the lens heater/cooler 337, etc.) In various implementations, such temperature adjustments may, in particular, be made for relatively large delta temperature changes (e.g., for large $\Delta T_{amb} \geq 15$ degrees C.).

Figure 7:
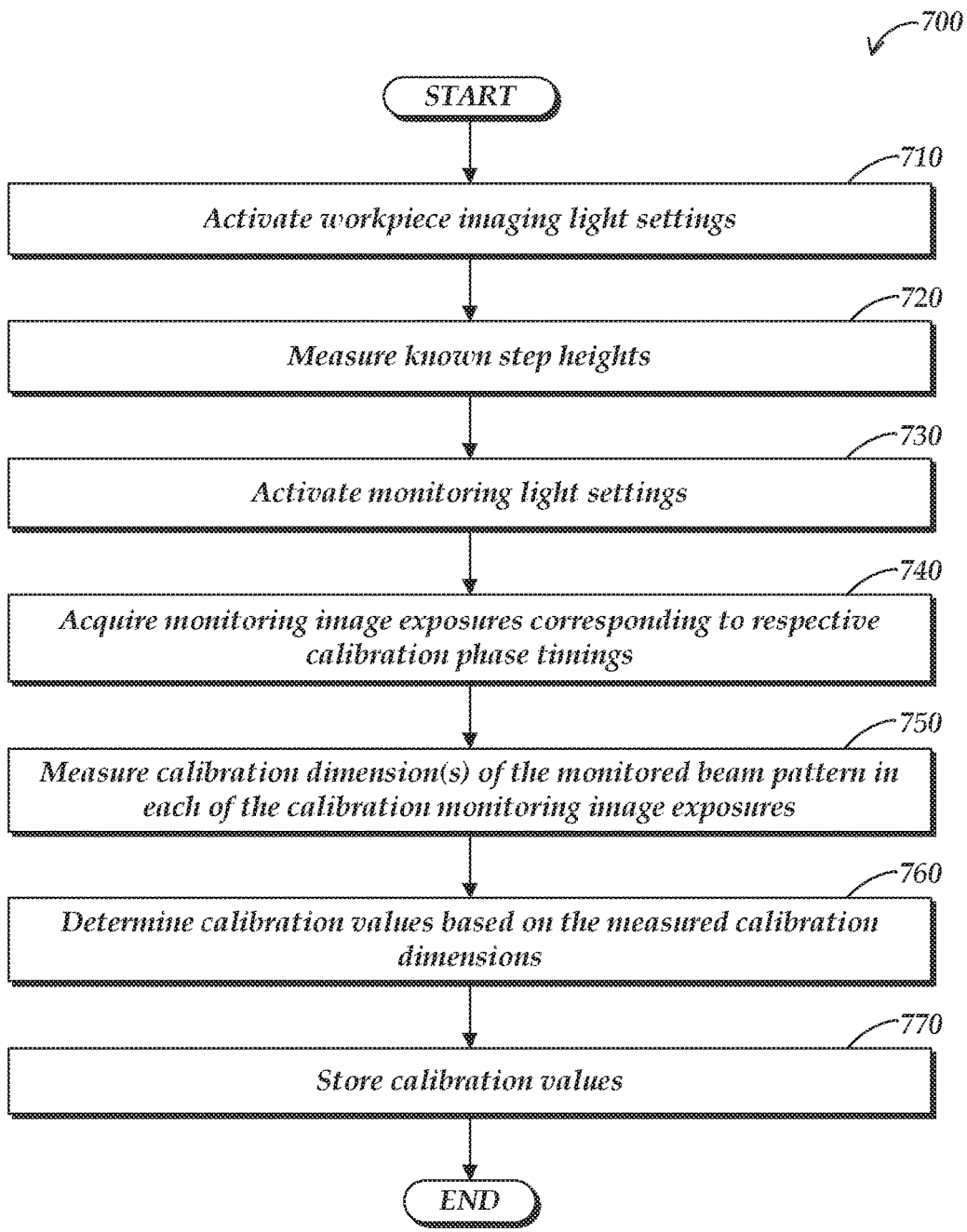
FIG. 7 is a flow diagram illustrating an exemplary implementation of a routine for determining and storing calibration values such as those used in the analysis of FIG. 6.

FIG. 7 is a flow diagram illustrating an exemplary implementation of a routine 700 for determining and storing calibration values such as those used in the analysis of FIG. 6. At block 710, workpiece imaging light settings are activated. As described above, in various implementations the workpiece imaging light settings may include activating a workpiece imaging light source (e.g., coaxial light source 330), and deactivating a monitoring light source (e.g., LED light source 386S).

At block 720, known step heights are measured utilizing specified calibration conditions. For example, a calibration object with known step heights may be utilized for determining the calibration values under specified conditions (e.g., assembly conditions, etc.) In various implementations, such specified conditions may include a specified steady-state temperature (e.g., T=20 degrees C.+/−0.25 degrees C.), with a specified objective lens 350 (e.g., a 2.5× magnification objective lens) and for which the VFL lens 370 may be operated at a specified frequency (e.g., 70 kHz), for which a +/−1 diopter may result in a specified Z scan range (e.g., a Z scan range of approximately 0.4 mm to −0.4 mm). In such a configuration, a calibration object may be provided that has steps with three known Z step heights including a lowest level corresponding to −0.4 mm, a mid step height corresponding to 0.0 mm, and an upper step height corresponding to +0.4 mm. In such a configuration, with respect to the phase timings that at least approximately correspond to each of the Z step height measurements, the 0 degree phase timing may correspond to the +0.4 mm Z step height, the 90 degree phase timing may correspond to the 0.0 mm Z step height, and the 180 degree phase timing may correspond to the −0.4 mm Z step height.

In various implementations, the process of measuring the step heights may include determining a desired amplitude A for the VFL lens, for which a contrast may be measured from a region of interest in each workpiece image exposure at each step height corresponding to the 0 degree, 90 degree and 180 degree phase timings. Techniques for measuring contrast in regions of interest are known in the art. In one specific example of implementation, the amplitude A (PZT Vp-p) may be iterated in order to determine a maximum region of interest contrast $C_{max}$, such as may occur at a final determined amplitude A* for the VFL lens as modulated over the range between the 0 degree phase timing and the 180 degree phase timing.

At block 730, monitoring light settings are activated. As described above, the monitoring light settings may include activating a monitoring light source (e.g., light source 386S) and deactivating a workpiece imaging light source (e.g., light source 330). At block 740, monitoring image exposures are acquired corresponding to the respective calibration phase timings. In one specific example implementation, in accordance with the example configurations described above with respect to FIGS. 4-6, the amplitude A* for the VFL lens may be utilized to acquire three monitoring image exposures corresponding to the 0 degree, 180 degree and 90 degree phase timings.

At block 750, calibration dimensions of the monitored beam pattern images are measured in each of the calibration monitoring image exposures. In various implementations, the measured calibration dimensions may correspond to the measured diameters of each of the monitored beam pattern images (e.g., calibration dimensions D1*, D2* and D3* may be measured, similar to the dimensions D1, D2 and D3 of FIGS. 5A-5C). At block 760, calibration values are determined based on the measured calibration dimensions. In one specific example implementation, similar to the determinations described above with respect to FIG. 6, the calibration value D12* may be determined according to the following equation:

$$D12^* = (D1^* - D2^*) \qquad \text{(Eq. 2)}$$

The calibration value D3* may simply correspond to the measured calibration dimension D3*. At block 770, the calibration values (e.g., D12* and D3*) are stored.

While preferred implementations of the present disclosure have been illustrated and described, numerous variations in the illustrated and described arrangements of features and sequences of operations will be apparent to one skilled in the art based on this disclosure. Various alternative forms may be used to implement the principles disclosed herein. In addition, the various implementations described above can be combined to provide further implementations. All of the U.S. patents and U.S. patent applications referred to in this specification are incorporated herein by reference, in their entirety. Aspects of the implementations can be modified, if necessary to employ concepts of the various patents and applications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled.

The invention claimed is:

1. A variable focal length (VFL) lens system, comprising:
   a VFL lens;
   a VFL lens controller that controls the VFL lens to periodically modulate an optical power of the VFL lens over a range of optical powers at an operating frequency;
   an objective lens that inputs workpiece light arising from a workpiece surface during a workpiece imaging mode and transmits the workpiece light along an imaging optical path that passes through the VFL lens;
   a camera that receives the workpiece light transmitted by the VFL lens along the imaging optical path during the workpiece imaging mode and provides a corresponding workpiece image exposure; and
   an optical power monitoring configuration comprising a monitoring beam generator comprising a light source and a beam pattern element that inputs light from the light source and outputs a monitored beam pattern, wherein:
      the optical power monitoring configuration transmits the monitored beam pattern along at least a portion of the imaging optical path to travel through the VFL lens to the camera during an optical power monitoring mode;
      the camera provides at least a first monitoring image exposure including the monitored beam pattern during at least a first phase timing of the periodic modulation of the VFL lens during the optical power monitoring mode; and
      a dimension of the monitored beam pattern in the first monitoring image exposure is related to an optical power of the VFL lens during the first phase timing.

2. The VFL lens system of claim 1, wherein the beam pattern element comprises an aperture element including an aperture that is located between the light source and the imaging optical path, and wherein during the optical power monitoring mode the light from the light source that passes through the aperture is output as the light of the monitored beam pattern which is directed along at least a portion of the imaging optical path to form an image of the monitored beam pattern in the first monitoring image exposure.

3. The VFL lens system of claim 1, wherein:
   the camera further provides at least a second monitoring image exposure including the monitored beam pattern during a second phase timing of the periodic modulation of the VFL lens during the optical power monitoring mode; and
   a dimension of the monitored beam pattern in the second monitoring image exposure is related to an optical power of the VFL lens during the second phase timing.

4. The VFL lens system of claim 3, wherein the first and second phase timings are approximately 180 degrees apart.

5. The VFL lens system of claim 4, wherein:
   the camera further provides at least a third monitoring image exposure including the monitored beam pattern during a third phase timing of the periodic modulation of the VFL lens during the optical power monitoring mode;
   a dimension of the monitored beam pattern in the third monitoring image exposure is related to an optical power of the VFL lens during the third phase timing; and
   the third phase timing is approximately halfway between the first and second phase timings as corresponding to approximately 90 degrees different than each of the first and second phase timings.

6. The VFL lens system of claim 3, wherein at least one dimension of the monitored beam pattern in the first and second monitoring image exposures is measured.

7. The VFL lens system of claim 6, further comprising at least one video tool that is utilized to perform the measurement of the at least one dimension of the monitored beam pattern in the first and second monitoring image exposures.

8. The VFL lens system of claim 6, wherein the at least one dimension includes at least a diameter of the monitored beam pattern in the first and second monitoring image exposures, and the measured diameters are used to determine at least one measured value, which is compared to at least one stored calibration value, and an adjustment to the operation of the VFL lens is made by the VFL lens controller based at least in part on a comparison of the at least one measured value to the at least one calibration value.

9. The VFL lens system of claim 6, wherein:
   the at least one dimension includes at least the diameter of the monitored beam pattern in the first and second monitoring image exposures;
   the measured diameters are further related to an optical magnification of the VFL lens during the phase timing or optical power corresponding to the first and second monitoring image exposures; and
   at least one of a stored optical magnification value or a physical component location that affects the optical magnification of the VFL lens system is adjusted based on an optical magnification determined based, at least in part, on the diameter of the monitored beam pattern in the first and second monitoring image exposures.

10. The VFL lens system of claim 3, wherein the light of the monitored beam pattern underfills a field of view of the camera during all phase timings of the periodic modulation of the VFL lens during the optical power monitoring mode.

11. The VFL lens system of claim 1, wherein the light source of the monitoring beam generator is a monitoring light source and the VFL lens system further comprises a workpiece imaging light source and a reflecting surface, the reflecting surface directing imaging source light from the workpiece imaging light source toward the workpiece surface during the workpiece imaging mode and transmitting workpiece light arising from the workpiece surface along the imaging optical path.

12. The VFL lens system of claim 11, wherein the optical power monitoring configuration further comprises a dichroic reflecting surface that reflects the light of the monitored beam pattern from the beam pattern element toward the reflecting surface, the reflecting surface directing the light of the monitored beam pattern along at least the portion of the imaging optical path to travel through the VFL lens to the camera during the optical power monitoring mode.

13. The VFL lens system of claim 12, wherein the light of the monitored beam pattern has a wavelength that is different than a wavelength of the imaging source light, and the dichroic reflecting surface primarily transmits rather than reflects any of the imaging source light that reaches the dichroic reflecting surface.

14. The VFL lens system of claim 1, wherein the VFL lens is included in a 4F imaging configuration that the imaging optical path passes through and which is utilized at least in part for imaging the workpiece surface during the workpiece imaging mode and which the light of the monitored beam pattern passes through during the optical power monitoring mode.

15. The VFL lens system of claim 1, wherein the workpiece imaging mode does not overlap with the optical power monitoring mode.

16. The VFL lens system of claim 1, wherein the VFL lens is a tunable acoustic gradient index of refraction lens.

17. An optical power monitoring configuration for use in a variable focal length (VFL) lens system, the VFL lens system comprising:
- a VFL lens;
- a VFL lens controller that controls the VFL lens to periodically modulate the optical power of the VFL lens over a range of optical powers at an operating frequency;
- an objective lens that inputs workpiece light arising from a workpiece surface during a workpiece imaging mode and transmits the workpiece light along an imaging optical path that passes through the VFL lens; and
- a camera that receives the workpiece light transmitted by the VFL lens along the imaging optical path during the workpiece imaging mode and provides a corresponding workpiece image exposure; and the optical power monitoring configuration comprising:
- a monitoring beam generator comprising a light source and a beam pattern element that is configured to input light from the light source and output a monitored beam pattern, wherein:
  the optical power monitoring configuration is configured to transmit the monitored beam pattern along at least a portion of the imaging optical path to travel through the VFL lens to the camera during an optical power monitoring mode such that the camera provides at least a first monitoring image exposure including the monitored beam pattern during at least a first phase timing of the periodic modulation of the VFL lens during the optical power monitoring mode, and a dimension of the monitored beam pattern in the first monitoring image exposure is related to an optical power of the VFL lens during the first phase timing.

18. The optical power monitoring configuration of claim 17, wherein the beam pattern element comprises an aperture element including an aperture that is located between the light source and the imaging optical path, and wherein during the optical power monitoring mode the light from the light source that passes through the aperture is output as the light of the monitored beam pattern which is directed along at least a portion of the imaging optical path to form an image of the monitored beam pattern in the first monitoring image exposure.

19. A computer implemented method for operating a variable focal length (VFL) lens system, the VFL lens system comprising a VFL lens, a VFL lens controller, an objective lens and a camera, the computer implemented method comprising:

under control of one or more computing systems configured with executable instructions, controlling the VFL lens to periodically modulate an optical power of the VFL lens over a range of optical powers at an operating frequency;

initiating a workpiece imaging mode, the workpiece imaging mode including utilizing workpiece imaging light settings and operating the camera to receive workpiece light transmitted by the VFL lens along an imaging optical path to provide at least one corresponding workpiece image exposure, wherein the imaging optical path includes the objective lens which is configured to input workpiece light arising from a workpiece surface and to transmit the workpiece light along the imaging optical path that passes through the VFL lens;

determining that an optical power monitoring mode is to be initiated;

initiating the optical power monitoring mode, the optical power monitoring mode including utilizing monitoring light settings and operating the camera to receive a monitored beam pattern and to provide a plurality of monitoring image exposures including the monitored beam pattern, wherein an optical power monitoring configuration comprises a monitoring beam generator comprising a monitoring light source utilized for the monitoring light settings and a beam pattern element that inputs light from the monitoring light source and outputs the monitored beam pattern, and the optical power monitoring configuration is configured to transmit the monitored beam pattern along at least a portion of the imaging optical path to travel through the VFL lens to the camera during the optical power monitoring mode, and each of the monitoring image exposures corresponds to a respective phase timing of the periodic modulation of the VFL lens, and at least one dimension of the monitored beam pattern in each respective monitoring image exposure is related to an optical power of the VFL lens during the respective phase timing;

measuring the at least one dimension of the monitored beam pattern in each of the monitoring image exposures;

determining that at least one adjustment to the operation of the VFL lens will be made based at least in part on the measured at least one dimension of the monitored beam pattern in each of the monitoring image exposures; and performing the at least one adjustment to the operation of the VFL lens.

20. The computer implemented method of claim 19, wherein the measuring includes utilizing a video tool to measure the at least one dimension of the monitored beam pattern in each of the monitoring image exposures.

* * * * *